(12) United States Patent
Kovach et al.

(10) Patent No.: US 10,028,834 B2
(45) Date of Patent: Jul. 24, 2018

(54) ADJUSTABLE PROSTHETIC ANATOMICAL DEVICE HOLDER AND HANDLE FOR THE IMPLANTATION OF AN ANNULOPLASTY RING

(75) Inventors: Melinda K. Kovach, Plymouth, MN (US); Susan E. Clegg, White Bear Lake, MN (US); Benjamin E. Morris, Jeffersonville, IN (US); Gregory R. Furnish, Louisville, KY (US); Eric E. Bielefeld, Floyds Knobs, IN (US); Simon McKnight Furnish, Louisville, KY (US)

(73) Assignee: St. Jude Medical, Inc., St. Paul, MN (US)

( * ) Notice: Subject to any disclaimer, the term of this patent is extended or adjusted under 35 U.S.C. 154(b) by 475 days.

(21) Appl. No.: 13/982,612

(22) PCT Filed: Jan. 31, 2012

(86) PCT No.: PCT/US2012/023359
§ 371 (c)(1),
(2), (4) Date: Dec. 19, 2013

(87) PCT Pub. No.: WO2012/106354
PCT Pub. Date: Aug. 9, 2012

(65) Prior Publication Data
US 2014/0142690 A1 May 22, 2014

Related U.S. Application Data

(60) Provisional application No. 61/438,129, filed on Jan. 31, 2011.

(51) Int. Cl.
*A61F 2/24* (2006.01)
*B25G 1/04* (2006.01)
(Continued)

(52) U.S. Cl.
CPC .......... *A61F 2/2466* (2013.01); *A61F 2/2445* (2013.01); *A61F 2/2496* (2013.01);
(Continued)

(58) Field of Classification Search
CPC ...... A61F 2/243; A61F 2/2427; A61F 2/2442; A61F 2/2445; A61F 2/2466
See application file for complete search history.

(56) References Cited

U.S. PATENT DOCUMENTS 4,099,518 A 7/1978 Baylis et al.
5,257,632 A 11/1993 Turkel et al.
(Continued)

FOREIGN PATENT DOCUMENTS

DE 202005013648 U1 3/2006
WO 0150985 A1 7/2001
(Continued)

OTHER PUBLICATIONS

International Search Report for Application No. PCT/US2012/023309 dated Jun. 20, 2012.
(Continued)

*Primary Examiner* — Tuan V Nguyen
(74) *Attorney, Agent, or Firm* — Lerner, David, Littenberg, Krumholz & Mentlik, LLP

(57) ABSTRACT

An adjustable prosthetic anatomical holder system may include an adjustable annuloplasty ring, a ring holder, and a positioning handle. The adjustable annuloplasty ring holder facilitates placement and adjustment of the annuloplasty ring during a cardiac surgical procedure. An optional positioning handle holds the adjustable annuloplasty ring during placement and suturing of the ring. The ring holder is constructed from two members that are slidably fit together in telescopic arrangement to accommodate adjustment of the ring size.

31 Claims, 9 Drawing Sheets

(51) Int. Cl.
*B25G 3/18* (2006.01)
*B25B 15/02* (2006.01)
*B25B 23/142* (2006.01)
*A61B 5/107* (2006.01)

(52) U.S. Cl.
CPC ............ *B25B 15/02* (2013.01); *B25B 23/142* (2013.01); *B25G 1/046* (2013.01); *B25G 3/18* (2013.01); *A61B 5/1076* (2013.01); *A61F 2/2448* (2013.01); *A61F 2250/001* (2013.01); *A61F 2250/006* (2013.01); *A61F 2250/0065* (2013.01); *A61F 2250/0089* (2013.01); *A61F 2250/0097* (2013.01)

(56) References Cited

U.S. PATENT DOCUMENTS

| | | |
|---|---|---|
| 6,019,776 A | 2/2000 | Preissman et al. |
| 6,086,543 A | 7/2000 | Anderson et al. |
| 6,090,138 A | 7/2000 | Chasak et al. |
| 6,110,128 A | 8/2000 | Andelin et al. |
| 6,117,108 A | 9/2000 | Woehr et al. |
| 6,189,422 B1 | 2/2001 | Stihl |
| 6,221,047 B1 | 4/2001 | Greene et al. |
| 6,554,778 B1 | 4/2003 | Fleming, III |
| 6,616,630 B1 | 9/2003 | Woehr et al. |
| 6,645,213 B2 | 11/2003 | Sand et al. |
| 6,689,102 B2 | 2/2004 | Greene |
| 6,893,184 B2 | 5/2005 | Mills et al. |
| 7,175,660 B2 | 2/2007 | Cartledge et al. |
| 7,442,207 B2 | 10/2008 | Rafiee |
| 7,455,690 B2 | 11/2008 | Cartledge et al. |
| 7,658,725 B2 | 2/2010 | Bialecki et al. |
| 7,850,620 B2 | 12/2010 | Miller et al. |
| 8,486,024 B2 | 7/2013 | Steube |
| 8,574,289 B2 | 11/2013 | Cartledge et al. |
| 8,628,497 B2 | 1/2014 | Finnestad et al. |
| 8,715,250 B2 | 5/2014 | Tremblay |
| 8,758,372 B2 | 6/2014 | Cartledge et al. |
| 8,778,021 B2 | 7/2014 | Cartledge |
| 8,834,422 B2 | 9/2014 | Walker et al. |
| 9,107,750 B2 | 8/2015 | Cartledge et al. |
| 9,138,316 B2 | 9/2015 | Bielefeld |
| 2001/0049558 A1* | 12/2001 | Liddicoat .............. A61F 2/2445 623/2.36 |
| 2003/0125715 A1* | 7/2003 | Kuehn .................. A61B 19/26 606/1 |
| 2003/0191416 A1 | 10/2003 | Rosenman et al. |
| 2004/0034410 A1* | 2/2004 | Holmberg ............ A61F 2/2466 623/2.11 |
| 2005/0027263 A1 | 2/2005 | Woehr et al. |
| 2005/0222665 A1 | 10/2005 | Aranyi |
| 2005/0222678 A1 | 10/2005 | Lashinski et al. |
| 2005/0257345 A1 | 11/2005 | Mitchell et al. |
| 2006/0064164 A1 | 3/2006 | Thelen et al. |
| 2006/0217803 A1 | 9/2006 | Ingle et al. |
| 2006/0233602 A1 | 10/2006 | Merems |
| 2006/0241748 A1 | 10/2006 | Lee et al. |
| 2007/0239108 A1 | 10/2007 | Albrecht et al. |
| 2008/0033545 A1* | 2/2008 | Bergin ................. A61F 2/2427 623/2.11 |
| 2008/0045857 A1 | 2/2008 | Miller et al. |
| 2008/0287859 A1 | 11/2008 | Miller et al. |
| 2008/0308600 A1 | 12/2008 | Kana |
| 2009/0093877 A1* | 4/2009 | Keidar .................. A61F 2/2448 623/2.11 |
| 2009/0125102 A1 | 5/2009 | Cartledge et al. |
| 2009/0192605 A1* | 7/2009 | Gloss .................... A61B 5/1076 623/2.11 |
| 2009/0194446 A1 | 8/2009 | Miller et al. |
| 2009/0259305 A1* | 10/2009 | Lane ..................... A61F 2/2427 623/2.11 |
| 2009/0266367 A1 | 10/2009 | Ziv et al. |
| 2009/0275994 A1 | 11/2009 | Phan et al. |
| 2010/0010538 A1 | 1/2010 | Juravic et al. |
| 2010/0011535 A1 | 1/2010 | Schuelke |
| 2010/0016804 A1 | 1/2010 | Muskatello et al. |
| 2010/0076503 A1 | 3/2010 | Beyar et al. |
| 2010/0161047 A1 | 6/2010 | Cabiri |
| 2010/0168675 A1 | 7/2010 | Cindrich et al. |
| 2010/0211166 A1 | 8/2010 | Miller et al. |
| 2010/0222746 A1 | 9/2010 | Burkholz |
| 2010/0241222 A1* | 9/2010 | Ruyra Baliarda .... A61F 2/2445 623/2.37 |
| 2011/0000347 A1 | 1/2011 | Stark |
| 2011/0015617 A1 | 1/2011 | Chesnin et al. |
| 2011/0066231 A1* | 3/2011 | Cartledge ............ A61B 17/068 623/2.11 |
| 2011/0082387 A1 | 4/2011 | Miller et al. |
| 2011/0190879 A1 | 8/2011 | Bobo et al. |
| 2011/0202130 A1 | 8/2011 | Cartledge et al. |
| 2011/0295262 A1 | 12/2011 | Germain et al. |
| 2011/0301551 A1 | 12/2011 | Koehler et al. |
| 2012/0065590 A1 | 3/2012 | Bierman et al. |
| 2012/0090863 A1 | 4/2012 | Puzio et al. |
| 2012/0136436 A1 | 5/2012 | Cabiri et al. |
| 2012/0144626 A1 | 6/2012 | Lanz |
| 2013/0006232 A1 | 1/2013 | Pellegrino et al. |
| 2013/0116693 A1 | 5/2013 | Nelson et al. |
| 2014/0074226 A1 | 3/2014 | Bielefeld et al. |
| 2014/0213931 A1 | 7/2014 | Lee |
| 2015/0142048 A1 | 5/2015 | Coleman et al. |
| 2015/0150541 A1 | 6/2015 | Fumex et al. |
| 2015/0230823 A1 | 8/2015 | Morgan et al. |
| 2015/0290430 A1 | 10/2015 | Koehler et al. |
| 2016/0000017 A1 | 1/2016 | Pringnitz |

FOREIGN PATENT DOCUMENTS

| | | | |
|---|---|---|---|
| WO | 01049245 A2 | 7/2001 | |
| WO | WO 2008/085814 * | 1/2008 | ........... A61B 17/068 |
| WO | 2008/085814 A2 | 7/2008 | |
| WO | 2008097999 A2 | 8/2008 | |
| WO | 2009126629 A1 | 10/2009 | |
| WO | 2010014671 A1 | 2/2010 | |
| WO | 2010073246 A2 | 7/2010 | |

OTHER PUBLICATIONS

International Search Report for Application No. PCT/US2012/023340 dated Jun. 4, 2012.
International Search Report and Written Opinion for Application No. PCT/US2012/023359 dated May 11, 2013.
International Search Report for Application No. PCT/US/2012/023349 dated Jun. 18, 2012.
International Search Report for Application No. PCT/US2012/023333 dated May 10, 2012.
Extended European Search Report for Application No. EP16181026.2 dated Oct. 27, 2016.

* cited by examiner

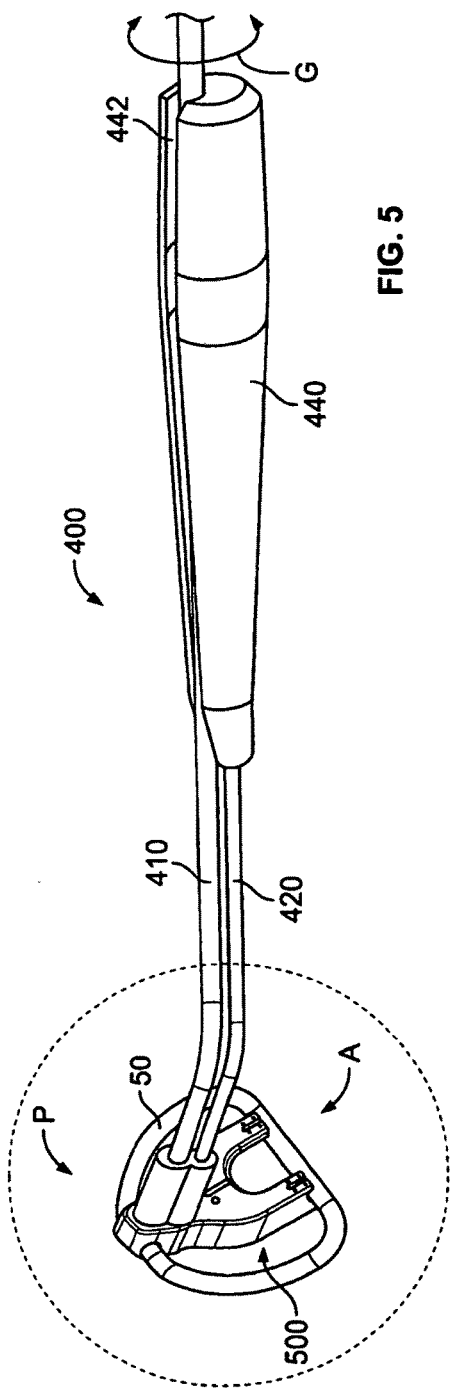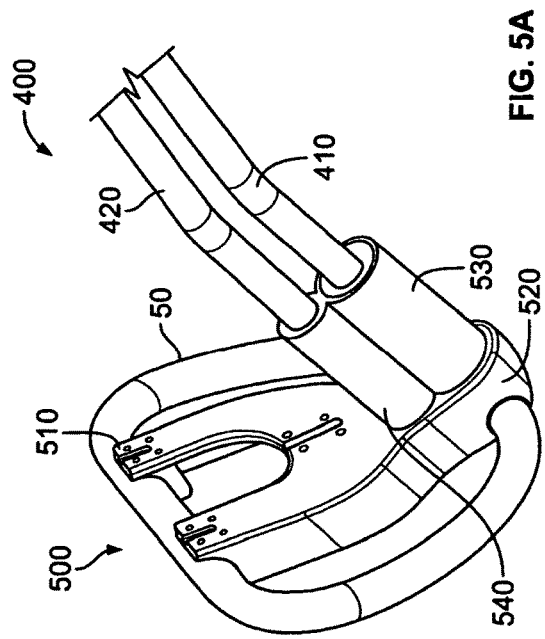
FIG. 5
FIG. 5A

ADJUSTABLE PROSTHETIC ANATOMICAL DEVICE HOLDER AND HANDLE FOR THE IMPLANTATION OF AN ANNULOPLASTY RING

CROSS-REFERENCE TO RELATED APPLICATIONS

The present application is a national phase entry under 35 U.S.C. § 371 of International Application No. PCT/US2012/023359 filed Jan. 31, 2012, published in English, which claims the benefit of the filing date of U.S. Provisional Patent Application No. 61/438,129 filed Jan. 31, 2011, the entire disclosure of both of which are hereby incorporated herein by reference.

BACKGROUND OF THE INVENTION

The present disclosure generally relates to surgical devices for use in cardiac surgery, and more specifically to prosthetic anatomical devices for facilitating the implantation of an annuloplasty ring, e.g., a mitral valve ring, for the correction of a heart valve disorder, e.g., mitral insufficiency.

The mitral valve is a dual-flap valve in the heart that lies between the left atrium and the left ventricle. In a normally functioning heart, oxygenated blood passes from the left atrium through the opened mitral valve and into the left ventricle when the left ventricle is in a relaxed state. In some individuals, the mitral valve does not function normally.

Mitral insufficiency, which is also known as mitral regurgitation, is a common cardiac abnormality in which the mitral valve does not close properly. With mitral insufficiency, the mitral valve does not fully close and some blood leaks back into the left atrium when the left ventricle contracts. The extra volume of blood that the heart must pump to compensate for the regurgitated blood creates undue strain on the left ventricle. The undue strain on the left ventricle may eventually wear out the heart and lead to death.

Mitral valve annuloplasty is an approach for treating mitral insufficiency by reconstructing the mitral valve. In mitral valve annuloplasty, the leaflets of the mitral valve annulus are reconstructed to reestablish the size and shape of the normal mitral valve annulus. Such an annuloplasty most commonly incorporates the use of a mitral annuloplasty ring that is implanted on the mitral valve annulus.

Examples of an adjustable annuloplasty ring are disclosed in United States Patent Application Publication No. 2011/0066231, the entire disclosure of which is incorporated herein by reference. The disclosed annuloplasty ring includes an adjustment assembly for expanding or contracting the size of the opening formed by the ring. A suitable tool is also disclosed to engage the adjustment assembly to enable adjustment of the annuloplasty ring in situ once implanted into a patient.

Various annuloplasty ring holders have been devised to assist in handling and implanting annuloplasty rings, e.g., mitral valve rings. However, a continuing need exists for holders and other surgical devices to facilitate handling and implanting annuloplasty rings, e.g., mitral valve rings.

BRIEF SUMMARY OF THE INVENTION

The present disclosure is generally related to an adjustable prosthetic anatomical system and devices to enable the in situ adjustment of an annuloplasty ring or other prosthetic anatomical device after being implanted into a patient. In an embodiment, the adjustable prosthetic anatomical system includes an adjustable annuloplasty ring, e.g., an adjustable mitral ring. The adjustable annuloplasty ring includes an anterior region and a posterior region. The ring is transitionable between a first diameter and a second diameter, as well as to intermediate diameters between the first and second diameters. The adjustable prosthetic anatomical system also includes a holder, which is operably attachable to the adjustable annuloplasty ring and can adjust in situ to a suitable length corresponding to the diameter of the ring.

The holder includes a first or posterior member and a second or anterior member. The first member is operably attachable to the posterior region of the ring. The second member is operably attachable to the anterior region of the ring. In an embodiment, suture may be used to secure each of the first and second members to respective regions of the annuloplasty ring. In an embodiment, the first and second members are slideably movable relative to one another in telescopic relationship along one axis of the holder, proximally or distally, along a common plane. The first and/or second members may be formed from a transparent or substantially clear material, e.g., a transparent plastic or polymer (e.g., polysulfone) to facilitate a substantially unobstructed view of the patient's valve (not shown) through the holder.

In an embodiment, the adjustable prosthetic anatomical system may include an adjustment tool including an elongated shaft that is operably engagable with the ring to effect transitioning of the ring between the first and second diameters. The holder may include a neck member that extends from the first member. The neck member may include a channel for the reception of the elongated shaft of the adjustment tool. The channel may define a U-shape. The holder may be detachable from the ring while the adjustment tool is operably engaged with the ring. In an embodiment, the neck member of the holder includes a U-shaped channel for the reception of the adjustment tool and another channel for the reception of a positioning tool. Suture may be placed around the neck to secure tools, e.g., the elongated shaft of the adjustment tool, within the U-shaped channel to inhibit separation. Such suture may be cut after completing the procedure if and when removal of the holder and/or placement tool is needed.

The first and second members of the holder may be selectively attached or detached from one another. In an embodiment, the first member defines an elongated slot along a longitudinal axis. The second member may include a pair of generally opposing tabs. The tabs may be capable of small deflections such that the tabs may be moved closer together from a first distance to a second distance, the first distance being greater than the second distance. The tabs may be resiliently biased toward the first distance to secure the first and second members together while permitting the first and second members to slide relative to one another along a common plane, thereby adjusting the overall length of the holder. The first and second members may be coupled together by a length of suture, thereby inhibiting loss of one of the first and second members in the event of separation of the first and second members.

In an embodiment, a holder may include a first member having a longitudinally extending channel and a second member having a longitudinally extending bar in which the bar is translatable through the channel to effect transitioning of the overall length of the holder between a first and second length, as well as to intermediate lengths between the first and second lengths. A length of suture may secure the first and second members together, thereby inhibiting loss of one of the first and second members during a procedure in the event that the first and second members are no longer in slidable connection with respect to one another. The length of suture may be placed on the underside of the holder to inhibit confusion between the length of suture and the attachment suture securing the holder to the ring.

In an embodiment, the first member may include a plurality of generally opposing tabs which create a longitudinally extending channel and a second member may have a longitudinally extending bar with a protrusion. The tabs may be capable of small deflections such that the tabs may be moved further apart from a first distance to a second distance, the second distance being greater than the first distance, for example when the region of the second member bar with the protrusion is passed between the opposing tabs of the first member. The bar is translatable through the channel to effect transitioning of the overall length of the holder between a first and second length, as well as to intermediate lengths between the first and second lengths. The opposing tabs may be resiliently biased toward the first distance to inhibit separation of the first and second members after they have been coupled.

During use of the aforesaid embodiments, each of the first and second members of the holder is secured to the annuloplasty ring, e.g., mitral valve ring, by one or more lengths of attachment suture. One or both of the first and second members may include one or more cutting blocks to indicate cutting location and facilitate cutting of the attachment suture to release the holder from the ring. The cutting blocks may be axially aligned to facilitate cutting of multiple attachment sutures by a single stroke of a scalpel. In an embodiment, the attachment suture is retained, i.e., remains attached to the first and second members after it is cut or severed.

In an embodiment, the first member of the holder includes a neck member. The neck member may extend from one end of the first member and may facilitate handling of the holder. The neck member may include a channel configured and adapted for the reception of an adjustment tool, which is configured and adapted to effect transitioning of the ring between the first and second diameters, as well as to intermediate diameters between the first and second diameters. In an embodiment, the neck member may include a channel that is adapted and configured to receive an elongated shaft or rod of a positioning tool. The elongated shaft or rod of the positioning tool may be formed from a malleable or bendable material to facilitate desired orientation and placement of the holder and the ring.

In an embodiment, a positioning tool includes an elongated shaft that is operably coupled to or integrally formed with the distal end of a gripping section of a handle. The elongated shaft of the positioning tool may be integrally formed with a posterior or first member of a holder or may be operably attachable to a channel defined within a neck member of the first member. The gripping section of the handle may define a groove in which an elongated shaft of an adjustment tool may be placed to facilitate access to and engagement with an adjustment mechanism, such as a gear of the adjustable ring held by the ring holder. The elongated shaft of the adjustment tool may be rotatable within the groove, while other movement of the elongated shaft that might result in separation of the elongated shaft of the adjustment tool is inhibited. Suture may operably couple the elongated shaft of the adjustment tool to the handle.

The holders and handles described herein may be used for a single use, i.e., they may be disposed of after use.

In accordance with one embodiment of the invention, there is disclosed an adjustable prosthetic anatomical system comprising an adjustable prosthetic anatomical device including an anterior region and a posterior region, the device being transitionable between a first diameter and a second diameter; and a holder comprising: a first member operably attachable to the posterior region of the device; and a second member operably attachable to the anterior region of the device, wherein the first member and the second member are operably engagable with one another to move relative to one another to accommodate adjustment of the device between the first and second diameters.

In accordance with another embodiment of the invention, there is disclosed an adjustable prosthetic anatomical device holder comprising a first member operably attachable to a posterior region of an adjustable prosthetic anatomical device; and a second member operably attachable to an anterior region of the device, wherein the first member and the second member are engagable with one another to move relative to one another to accommodate adjustment of the device between a first and second diameter.

These and other features of the present disclosure will be more fully described with reference to the appended figures.

BRIEF DESCRIPTION OF THE DRAWINGS

By way of description only, embodiments of the present disclosure will be described herein with reference to the accompanying drawings, in which:

FIG. 5 is a perspective view of a handle in accordance with an embodiment of the present disclosure shown operably coupled to an annuloplasty ring holder and including a channel for the reception of the elongated shaft of the adjustment tool;

FIG. 5A is an enlarged view of the indicated area of FIG. 5;

DETAILED DESCRIPTION

Figure 1:
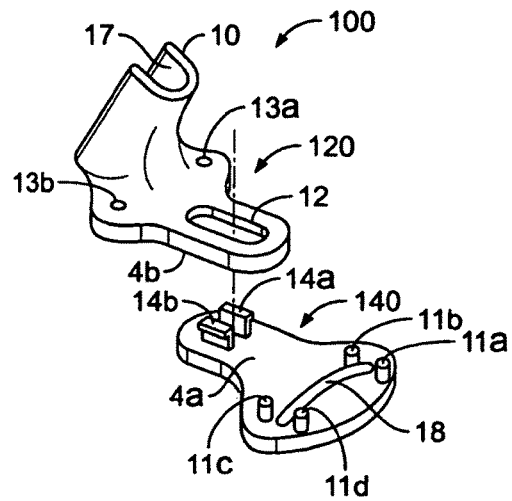
FIG. 1 is a perspective view of an annuloplasty ring holder in accordance with an embodiment of the present disclosure shown with parts separated.

Particular embodiments of the present disclosure will be described with reference to the accompanying drawings. In the figures and in the description that follow, in which like reference numerals identify similar or identical elements, the term "proximal" will refer to the end of the device that is closest to the operator during use, while the term "distal" will refer to the end of the device that is farthest from the operator during use. The term "posterior" will refer to a first region of the device, while the term "anterior" will refer to a second region of the device. The term "diameter" will refer generally to the size, shape, and/or opening of the adjustable prosthetic anatomical device, e.g., adjustable annuloplasty ring, which is adjusted in accordance with the invention as to be described.

Adjustable annuloplasty rings enable resizing of the ring during the surgical repair. Examples of an adjustable annuloplasty ring are disclosed in the aforesaid U.S. Pat. App. Pub. No. 2011/0066231. Disclosed herein are embodiments of annuloplasty ring holders and handles that facilitate handling of differently sized annuloplasty rings and adjustable annuloplasty rings including adjustable mitral valve rings.

An embodiment of an annuloplasty ring holder will now be described with reference to FIGS. 1-2B. An annuloplasty ring holder 100 may be used for holding any suitable prosthetic anatomical device such as an annuloplasty ring, e.g., a mitral ring, to facilitate placement of the annuloplasty ring during a surgical valve repair procedure, e.g., mitral valve annuloplasty. As shown best in FIG. 2B, the annuloplasty ring holder 100 is operably attachable to an adjustable annuloplasty ring 50. The annuloplasty ring holder 100 has an overall variable length L (FIG. 2B) that is adjustable to generally correspond with the variable diameter D of the ring 50.

Figure 2A:
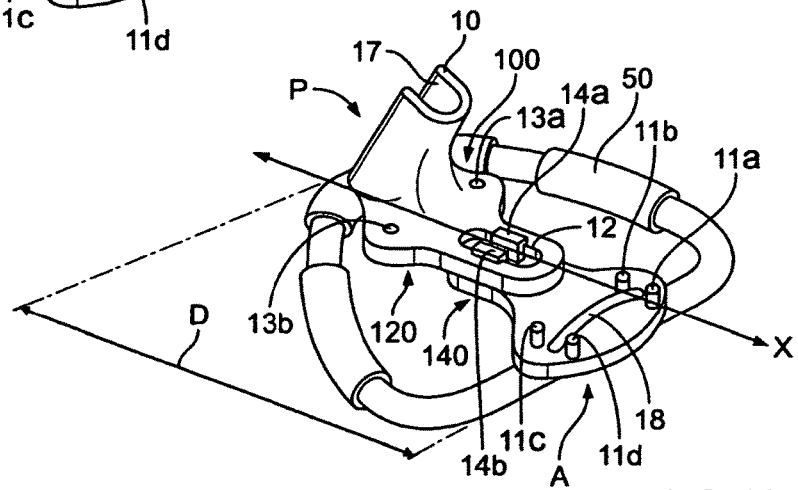
FIG. 2A is a perspective view of the annuloplasty ring holder of FIG. 1 shown relative to an adjustable annuloplasty ring.

The annuloplasty ring holder 100 includes first or posterior member 120 and second or anterior member 140 that are movable relative to one another along a common plane in one axial direction to adjust the overall length L of the annuloplasty ring holder 100 in a generally telescopic manner. The first member 120 and the second member 140 are secured to the corresponding regions of ring 50 so that the overall length L of the annuloplasty ring holder 100 is capable of changing as the diameter D of the ring 50 changes (FIGS. 2A-2B). The annuloplasty ring 50 defines a diameter D, which is adjustable, i.e., reduced or expanded, by actuating an adjustment mechanism such as a gear 52, e.g., by rotating a shaft operably coupled to the gear 52.

The first member 120 and the second member 140 are releasably attachable or securable to one another to facilitate sliding movement of the first member 120 with respect to the second member 140 along a generally common plane such as defined between facing surfaces 4a, 4b while inhibiting separation of the first member 120 from the second member 140. One of the first and second members 120, 140 includes one or more projecting tabs 14a, 14b that are releasably securable within a longitudinally extending slot 12 defined in the other one of the first and second members 120, 140, thereby permitting axial movement of the first and second members 120, 140 with respect to one another while inhibiting other movement of the first and second members 120, 140 with respect to one another. The first and second members 120, 140 may be formed from any suitable material including a transparent material, e.g., a transparent plastic or polymer, to facilitate a substantially unobstructed view of the patient's valve (not shown) through the holder 100.

Figure 2B:
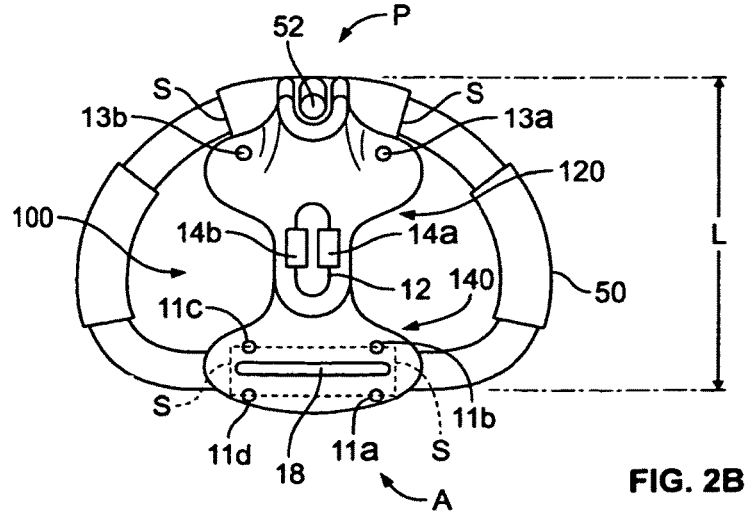
FIG. 2B is a top view of the annuloplasty ring holder of FIG. 1 shown secured to the adjustable annuloplasty ring of FIG. 2A.

As shown in FIGS. 1-2B, the second member 140 includes tab members 14a, 14b that function as a locking mechanism, flexing until passed through a longitudinally extending slot 12 defined within the first member 120. The tab members 14a, 14b engage the slot 12 in a snap-fit relationship and lips of the tab members 14a, 14b interact with a surface of the first member 120 to inhibit separation of the first and second members 120, 140.

The tab members 14a, 14b are capable of small deflections relative to one another and are biased toward an expanded state. Placement or removal of the tabs 14a, 14b from the slot 12 is facilitated by compressing the tabs 14a, 14b together, thereby decreasing the distance between the tabs 14a, 14b and permitting the tabs 14a, 14b to be inserted into or removed from the slot 12. In the expanded state, the tabs 14a, 14b are configured and adapted to engage a surface of the first member 120, the interaction of the tabs 14a, 14b with the surface of the first member 120 inhibits separation of the first and second members 120, 140.

When the tab members 14a, 14b are secured within the elongated slot 12, for example, by a snap-fit, the first member 120 and the second member 140 are slidable relative to one another along the longitudinal axis defined by the elongated slot 12, but separation of the first member 120 from the second member 140 is inhibited. After the first and second members 120, 140 are operatively coupled, sliding of the first member 120 with respect to the second member 140 along longitudinal axis x of the holder 100 effects a change in the length L of the holder 100 as desired to fit the holder 100 to the ring 50 and to accommodate size adjustment of the ring.

The first and second members 120, 140 may move relative to one another to adjust the overall length L of the holder 100 before or after attachment to the ring 50. Since the overall length L of the holder 100 and the diameter D of the ring 50 are adjustable, both the overall length L of the holder 100 and the diameter D of the ring 50 may be adjusted while the holder 100 remains attached to the ring 50.

Securing the holder 100 to the ring 50 will now be described with reference to FIGS. 2A-2B. The first member 120 is placed at the posterior region P of the ring 50, and the second member 140 is placed at the anterior region A of the ring 50. The first member 120 includes one or more apertures 13a, 13b that are each configured and adapted to receive attachment suture S therethrough around the ring 50 to secure the ring 50 to the first member 120. The second member 140 includes one or more apertures 11a-d through which attachment suture S may be placed to secure the second member 140 to the ring 50. As shown in FIGS. 2A-2B, a cutting block 18 runs between apertures 11a, 11b and apertures 11c, 11d such that the suture S may be cut with a single motion of a scalpel (not shown) to release the second member 140 from the ring 50. It is contemplated that the first member 120 may include one or more cutting blocks (not shown) substantially similar to cutting block 18 to indicate a suitable pre-determined location to cut the attachment suture S. To reduce the number of actions required to cut the attachment sutures S, the cutting block(s) may define a single channel or may be axially aligned, i.e., a single motion of a scalpel (not shown) may be used to cut multiple attachment sutures S. In an embodiment, after cutting the attachment suture S, the attachment suture remains attached to the first or second member 120, 140, respectively, to facilitate removal of the attachment suture S from the surgical site.

Because the tabs 14a, 14b "snap-fit" the second member 140 to the first member 120, the first member 120 and the second member 140 are inhibited from separating from one another during the procedure, including after the attachment suture S is cut from one or both of the first and second members 120, 140, respectively. This locking mechanism facilitates the removal of the assembled holder 100, including both the first and second members 120, 140, after placement of the ring 50. Removal of the first and second members 120, 140, respectively, is facilitated by having the first and second members 120, 140 coupled to each other in some fashion. For example, a single instrument (not shown) may grasp the assembled holder 120, 140 without having to grasp the first and second members 120, 140 separately. In addition, because the first and second members 120, 140 are each smaller in size than the diameter D of the ring 50, coupling of the first and second members 120, 140 inhibits the potential of one of the first and second members 120, 140 falling through the center of the ring 50 once the attachment suture S is cut or otherwise separated from the ring 50.

As shown in FIGS. 1-2B, the first member 120 includes an upstanding neck member 10 that extends proximally from the posterior region P of the first member 120. The neck member 10 may be integral with the other portions of the first member 120. The neck member 10 may be grasped by the surgeon to facilitate handling and manipulation of the first member 120. The neck member 10 may function as a handle, giving the surgeon or surgical assistant a place to grip the holder 100 to hold the ring 50 in a given position as implant sutures (not shown) are placed into the ring 50 to secure the ring 50 to the target location (not shown). The neck member 10 may be short to allow for a minimally invasive surgical procedure, or relatively long as might be used in an open sternotomy procedure.

The neck member 10 may include a channel 17 for the reception of an adjustment tool having an elongated shaft (not shown) that is configured and adapted to be operably coupled to ring 50, such as to the gear 52 of ring 50, to effect adjustment of the diameter D of the ring 50. The neck member 10 may be generally U-shaped such that the channel defined by the neck member 10 has a partially open perimeter. The U-shaped configuration of the neck member 10 facilitates detachment of the holder 100 from the ring 50 while the adjustment tool (not shown) remains operably coupled to the ring 50. In an embodiment, the adjustment tool (not shown) may be secured to the neck member 10 with suture to facilitate stabilization of the adjustment tool with respect to the neck member 10. In this regard, the neck member 10 may also be provided with one or more cutting blocks (not shown) to indicate where to cut the suture prior to removal of the adjustment tool.

Once the ring 50 is in the desired target location, the ring 50 may be sutured to the patient's tissue (not shown) to secure the ring 50 thereto. The holder 100 may also be modified to incorporate a positioning tool as to be described generally with reference to FIG. 5. By having the first and second members 120, 140 of the holder 100 disposed within the diameter D of the ring 50, access to the circumference of the ring 50 is facilitated, thereby providing greater suture access, i.e., space available for the surgeon to place implant sutures. In addition, as shown best in FIG. 2A, the first and second members 120, 140 of the holder 100 sit atop the upper or proximal surface of the ring 50, thereby inhibiting the potential of one of the first and/or second members 120, 140 falling through the ring 50 into the patient's valve (not shown) during removal of the holder 100 from the ring 50 subsequent to implantation of the ring 50. The diameter D of the ring 50, i.e., the anterior-posterior dimension, is adjustable in situ subsequent to implantation of the ring 50, as well as subsequent to the removal of the holder 100 from the surgical site. The adjustment of the ring 50 may occur either while the patient's heart is on cardiopulmonary bypass (CPB) and/or following removal of the CPB support, i.e., on a beating heart.

Figure 3A:
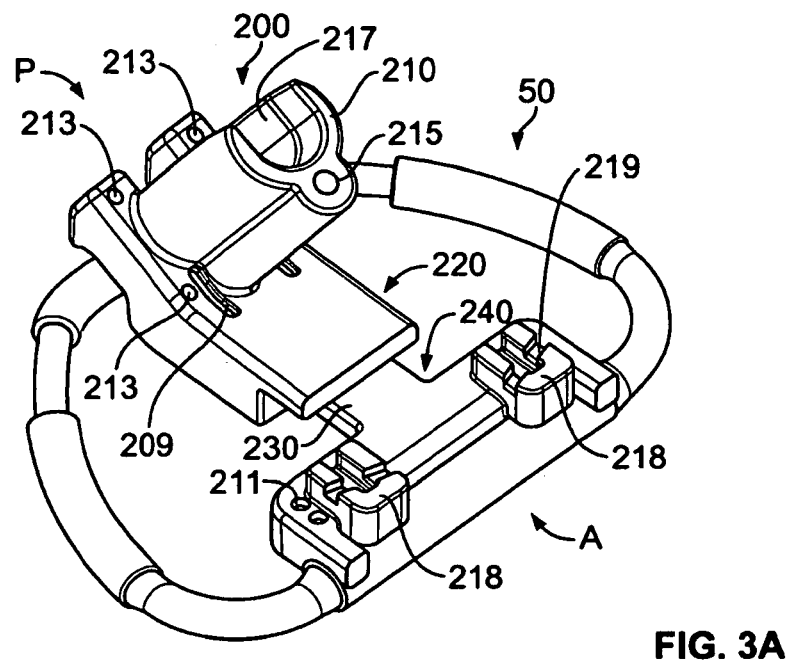
FIG. 3A is a top perspective view of an annuloplasty ring holder in accordance with another embodiment of the present disclosure shown operatively coupled to an adjustable annuloplasty ring.
Figure 3B:
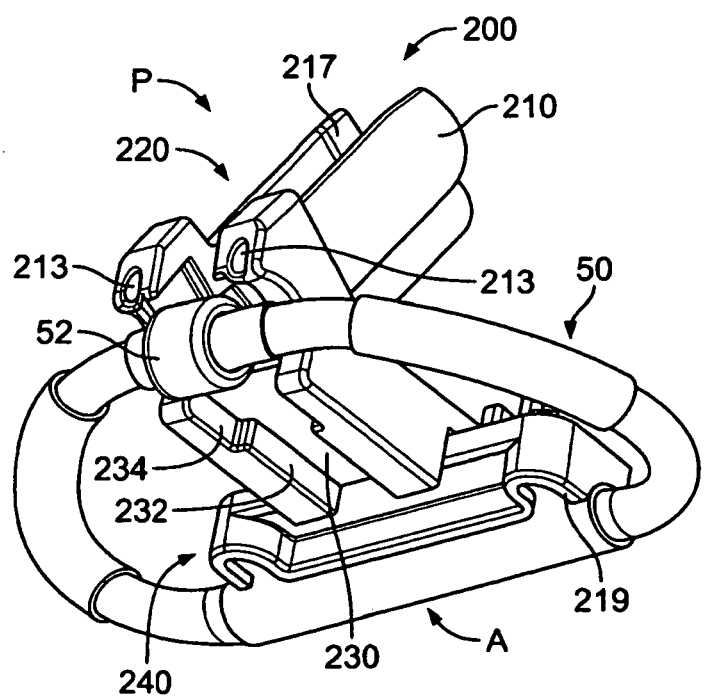
FIG. 3B is a bottom perspective view of the annuloplasty ring holder of FIG. 3A.

Another embodiment of a ring holder will now be described with respect to FIGS. 3A and 3B. As shown in FIG. 3A, an annuloplasty ring holder 200 is configured and adapted to be secured to any suitable annuloplasty ring, e.g., annuloplasty ring 50. The annuloplasty ring holder 200 includes a posterior or first member 220 and an anterior or second member 240 that are movable relative to one another along a common plane to adjust the longitudinal dimension or length of the holder 200 from the anterior region A to the posterior region P of the holder 200. The first and second members 220, 240 are positioned to rest upon an upper portion of the ring 50. By placing the first and second members 220, 240 of the holder 200 atop the ring 50, falling of the first and second members 220, 240 through the ring 50 is inhibited during removal of the holder 200 from the surgical site after implantation of the ring 50.

The first member 220 includes a channel 232 configured and adapted to receive a bar 230 of the second member 240 to facilitate sliding of the bar 230 relative to the first member and the adjustment of the overall length of the holder 200 as measured from the anterior region A to the posterior region P of the holder 200. The channel 232 may include a section 234 that engages a posterior region P of the bar 230 to limit the range within which the first and second members 220, 240 may axially translate with respect to one another. The channel 232 may include a groove within which the sides of the bar 230 are positioned, thereby inhibiting separation of the bar 230 from the channel 232, while permitting relative sliding movement.

The first member 220 is securable to the posterior region P of the ring 50, and the second member 240 is securable to the anterior region A of the ring 50. Securing of the first member 220 to the ring 50 is achievable by placing attachment suture through the apertures 213 defined within the first member 220 and around the ring 50. Securing of the second member 240 to the ring 50 is achievable by placing attachment suture through the apertures 211 defined within the second member 240 and around ring 50. The second member 240 includes cutting blocks 218 that each includes a channel 219. The channel 219 of one cutting block 218 is inline with the channel 219 of the other cutting block 218 such that a single stroke of a scalpel (not shown) may cut both attachment sutures securing the second member 240 to the anterior region A of the ring 50. In further embodiments, the first member 220 may include cutting blocks 209 to indicate the approximate location of the attachment suture. By indicating where to cut the attachment suture, the cutting blocks inhibit the possibility of inadvertently cutting suture that is utilized for purposes other than securing the holder 200 to the ring 50 and enable the attachment suture to remain attached to the first member 220 or the second member 240 to facilitate removal of the attachment suture from the surgical site.

The first member 220 includes a neck member 210 that defines a U-shaped channel 217 for the reception of an adjustment tool (not shown) that is configured and adapted to engage an adjustment mechanism of the ring 50, such as a gear 52 of the ring 50, to adjust, i.e., increase or decrease, the diameter of the ring 50. The neck member 210 provides a location at which a surgeon may grasp the holder 200. In addition, the U-shaped configuration of the channel 217, as previously described, facilitates removal of the holder 200 subsequent to implantation of the ring 50 while the adjustment tool (not shown) remains engaged with the gear 52 of the ring 50. The neck member 210 may also include a channel 215 adapted and configured for the reception of an elongated shaft of a positioning tool that facilitates the holding and manipulation of the holder 200. The elongated shaft of the positioning tool (not shown) may be formed from a malleable material or wire that may be bent to facilitate proper positioning and orientation of the ring 50 when it is attached to the holder 200. An example of a positioning tool will be described hereinafter, such as with reference to FIG. 5.

Another embodiment of an annuloplasty ring holder will now be described with reference to FIGS. 4A and 4B. The annuloplasty ring holder 300 shown in FIGS. 4A and 4B includes a posterior or first member 320 that is securable to the posterior region P of the ring 50 and an anterior or second member 340 that is securable to an anterior region A of the ring 50. The first and second members 320, 340 are slidable with respect to one another along a generally common plane to adjust the overall length of the holder 300 to facilitate securing of the holder 300 to the ring 50. The first member 320 is securable to the posterior region P of the ring 50 by placing attachment suture through apertures 313 defined within the first member 320. The second member 340 is securable to the anterior region A of the ring 50 by placing attachment sutures through apertures 311 defined within the second member 340. The second member 340 includes cutting blocks 318 including channels 319, the channel 319 in one cutting block 318 being aligned with the channel 319 in the other cutting block 318. The cutting blocks 318 indicate the location of the attachment suture, and the alignment of the channels 319 facilitates cutting of the attachment suture with a single scalpel stroke. The first member 320 may include cutting blocks 309 that indicate the location of the attachment suture securing the first member 320 to the posterior region P of the ring 50. Neck member 310 defines a U-shaped channel 317 in which an adjustment tool is placeable to engage the ring 50 and facilitate adjusting the diameter D of the ring 50. A channel 315 is configured and adapted to receive an elongated shaft of a positioning tool (not shown) to facilitate the positioning of the holder 300 and the corresponding positioning of the ring 50.

Figure 4A:
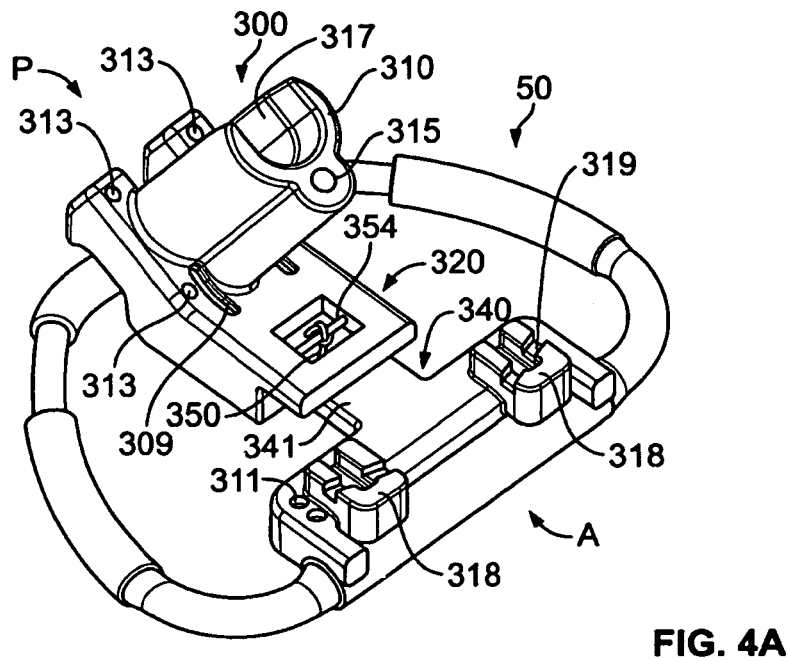
FIG. 4A is a perspective view of an annuloplasty ring holder in accordance with another embodiment of the present disclosure.
Figure 4B:
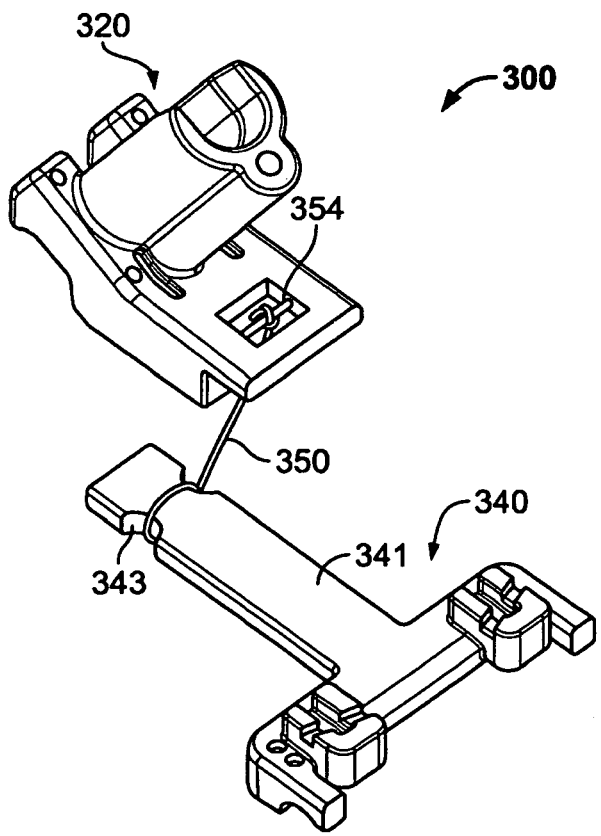
FIG. 4B is a perspective view of the annuloplasty ring holder of FIG. 4A shown with parts separated.

As shown in FIGS. 4A and 4B, the first member 320 is coupled to the second member 340 by a length of suture 350. The second member 340 includes a bar 341 that is translatable through a channel defined within the first member 320. The bar 341 may include a narrowed section 343 in one or more dimensions around which suture 350 is secured. The narrowed section 343 may inhibit a frictional interaction between the bar 341 and the channel defined within the first member 320, thereby inhibiting potential breakage of the suture 350. The suture 350 is secured to the first member 320 around a rod 354. In an embodiment, the suture 350 is not accessible from the upper surface of the first member 320 to inhibit inadvertent separation of the first and second members 320, 340. As shown in FIG. 4B, the suture 350 retains the first and second members 320, 340 in a coupled relationship even when the first and second members 320, 340 are not in a slidable relationship with one another. By coupling the first and second members 320, 340 by the suture 350, the potential that one of the first and second members 320, 340 may fall through the ring 50 after unsecuring the holder 300 from the ring 50 is lessened.

A holder handle 400 will now be described with reference to FIGS. 5 and 5A. The holder handle 400 facilitates both the adjustment of the adjustable annuloplasty ring 50 and the manipulation of an annuloplasty ring holder during placement and suturing of the ring 50 at the target site. Although the holder handle 400 is shown and described with reference to annuloplasty ring holder 500, it is to be understood that the holder handle may be used with any suitable annuloplasty ring holder including annuloplasty ring holders 200, 300, 900, 950 in which the ring holder includes one channel for the reception of an elongated shaft of an adjustment tool and another channel for the reception of an elongated shaft of a positioning tool. The holder 100 can also be modified to accept a holder handle 400.

The holder handle 400 includes a positioning rod 420 that is attachable to a holder 500 to facilitate desired positioning of the ring 50. The positioning rod 420 may be formed from a material that is malleable and/or bendable, e.g., nickel titanium alloy or annealed stainless steel. This allows adjustment of the angle of the handle 400 relative to the ring 50. As shown in FIGS. 5 and 5A, the rod 420 is positionable within a first channel 540 of a neck member 520 of the holder 500. The holder 500 can be constructed in accordance with any of the embodiments described herein. The holder handle 400 includes an elongated gripping section 440 to which rod 420 is attached. The gripping section 440 includes an axial U-shaped channel or groove 442 in which the elongated shaft 410 of an adjustment tool is positionable. The elongated shaft 410 of the adjustment tool may be loosely snap-fit into place, i.e., the elongated shaft 410 may be pressed within the groove 442 and the groove 442 may inhibit separation of the elongated shaft 410 from the gripping section 440 of the holder handle 400. Once placed within the groove 442, the elongated shaft 410 is capable of rotational movement as indicated by directional arrow G to enable adjustment of the prosthetic anatomical device to which the adjustment tool is coupled. The shaft may be rotated using, for example, the device disclosed in co-pending U.S. Application Ser. No. 61/527,801 filed on Aug. 26, 2011, the disclosure of which is incorporated herein.

Figure 6:
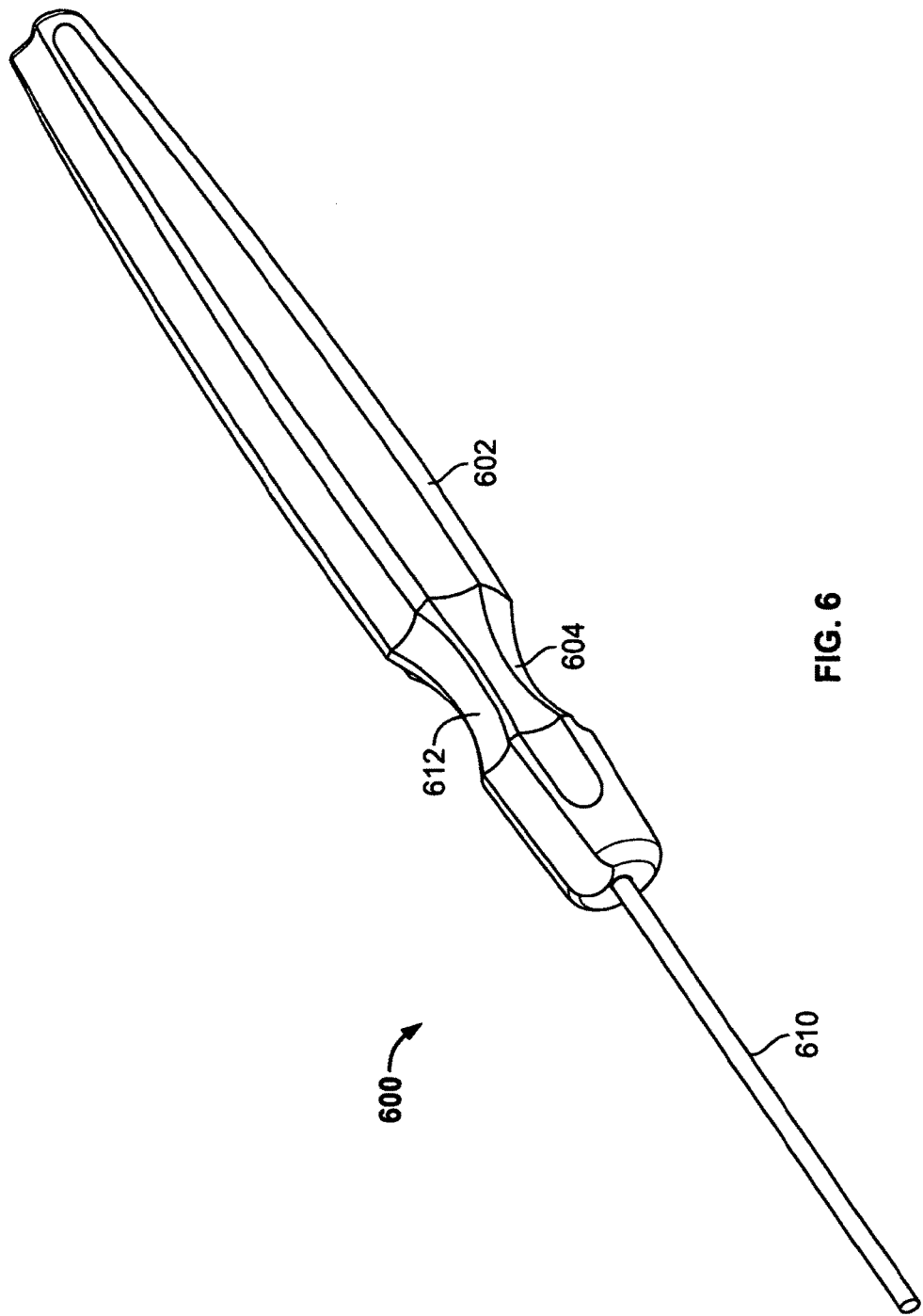
FIG. 6 is a perspective view of a handle in accordance with another embodiment of the present disclosure.

In another embodiment shown in FIG. 6, a holder handle 600 includes a gripping section 602 and a rod 610 that is placeable within a channel of a suitable ring holder, e.g., channel 215, 315, 540 of ring holders 200, 300, 500, respectively, to facilitate desired positioning of the ring holder and corresponding positioning and placement of the ring 50. The rod 610 may be malleable or bendable and may be formed from material capable of being bent, including but not limited to, by way of example, nickel titanium alloy or annealed stainless steel. A narrowed section 604 of the gripping section 602 may facilitate placement of a user's thumb or other finger for manipulation, e.g., rotation, of the gripping section 602. A groove 612 in gripping section 602 is configured and adapted for the reception of an elongated shaft of an adjustment tool that is suitable for engaging the adjustment mechanism of the ring 50 to effect suitable adjustment of the diameter D of the ring 50.

Figure 7:
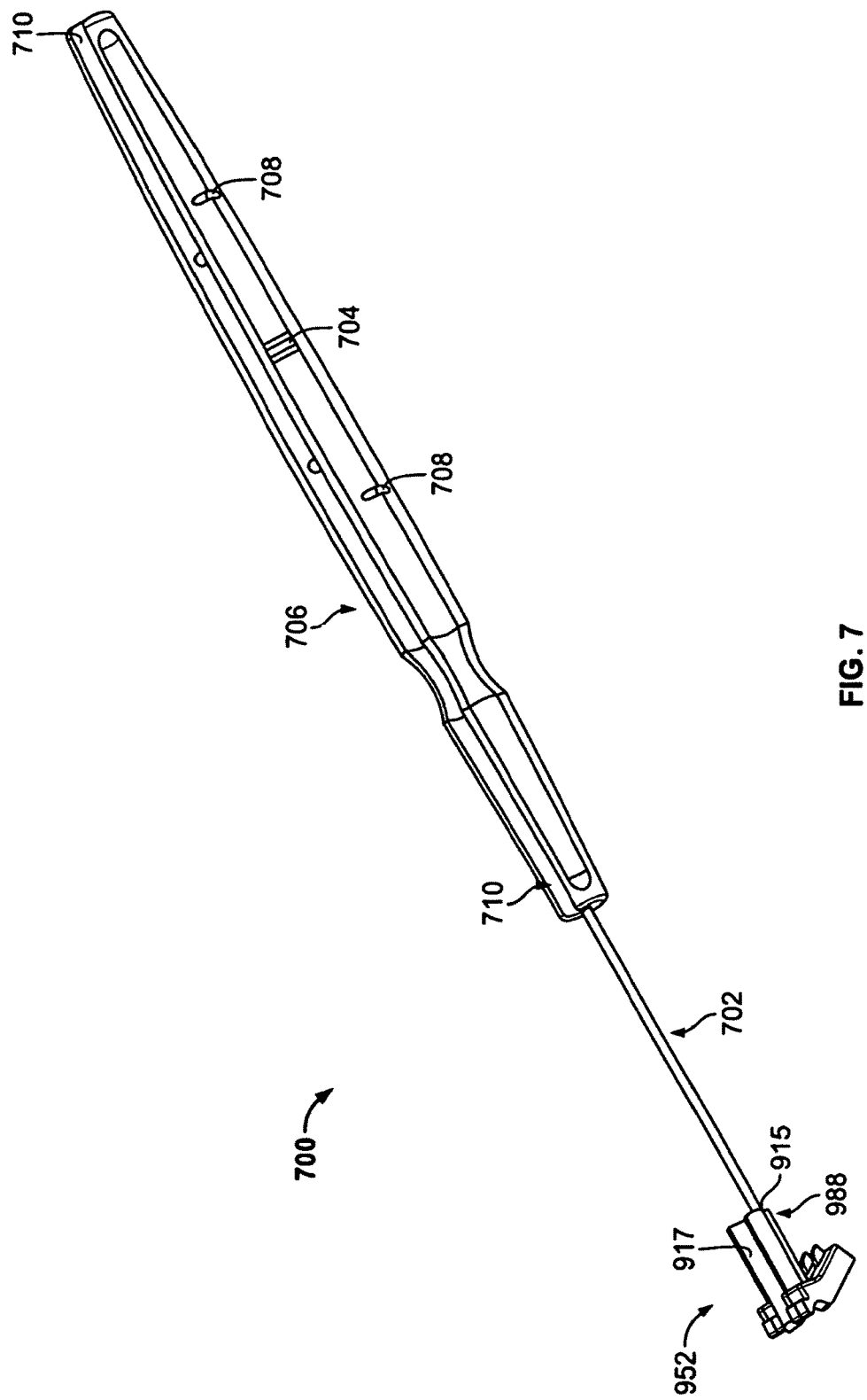
FIG. 7 is a perspective view of a handle assembly in accordance with another embodiment of the present disclosure and shown relative to a first member of the holder of FIG. 10.
Figure 10:
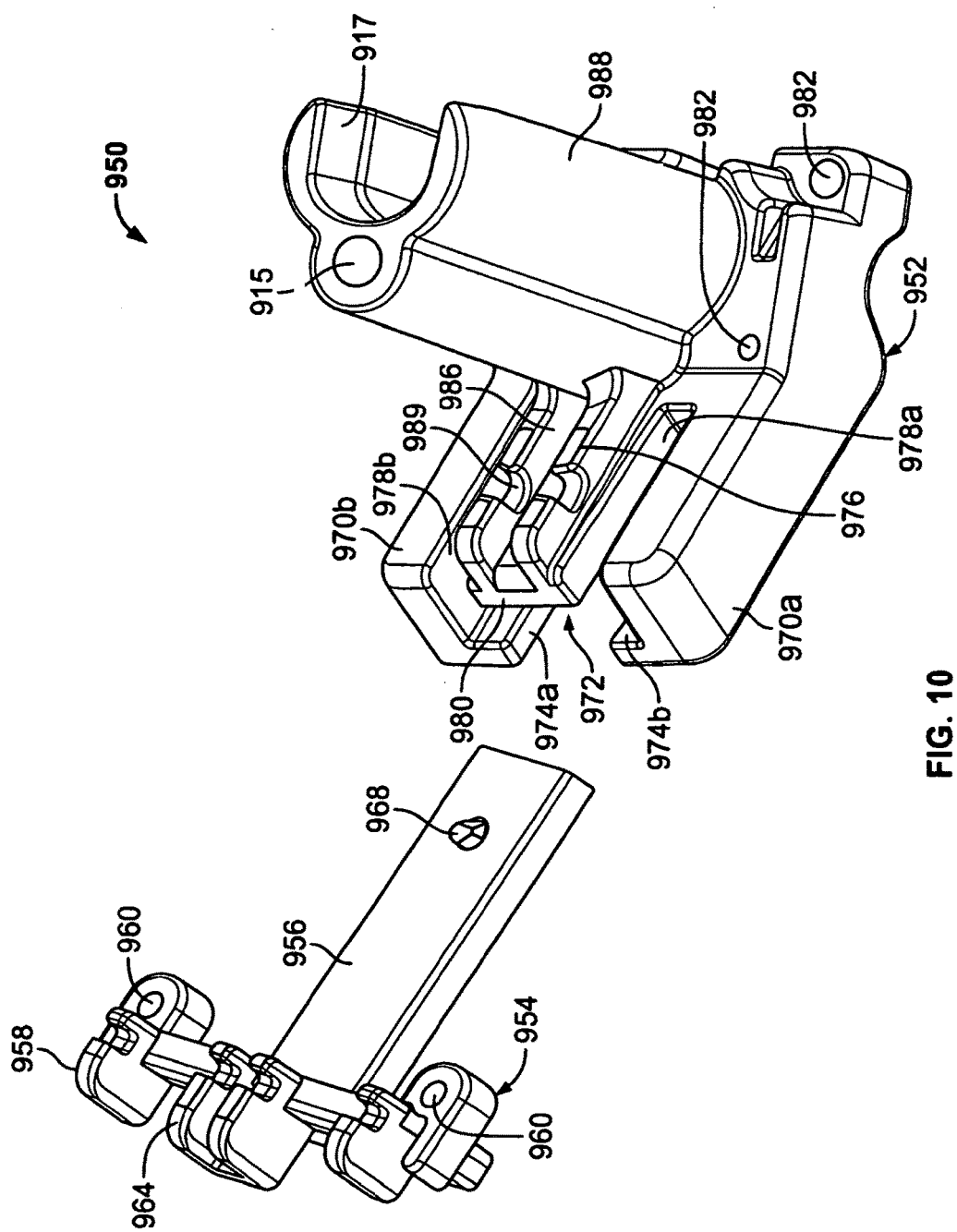
FIG. 10 is a perspective view of an annuloplasty ring holder in accordance with another embodiment of the present invention.

In an embodiment shown in FIG. 7, a holder handle assembly 700 includes a handle 706 that is operatively coupled to the first member 952 of the annuloplasty ring holder 950 (FIG. 10). As shown in FIG. 7, the first member 952 of the annuloplasty ring holder 950 includes a neck member 988 including channels 915, 917. The handle 706 includes a rod 702 that is operatively engaged with channel 915. In an embodiment, the first member 952 may be integrally formed with the handle 706. The elongated shaft 702 may be formed from a malleable wire, e.g., a wire having shape memory properties that is formed, for example, from a nickel titanium alloy or annealed stainless steel. The handle 706 defines a channel or groove 710 through which an elongated shaft of an adjustment tool (not shown) may be placed to be inserted through the channel 917 to engage the ring 50 and effect desired adjustment of the diameter D of the ring 50. The elongated shaft of the adjustment tool may be secured to the handle 706 by suture through apertures 708. A channel 704 may be defined in handle 706 to provide an indication of a cutting location and/or to receive a cutting tool, e.g., a scalpel, to facilitate separation of the handle 706 from the adjustment tool by cutting the suture extending across the channel. In an embodiment, the first member 952 and the handle 706 may be removed at the same time.

Figure 8:
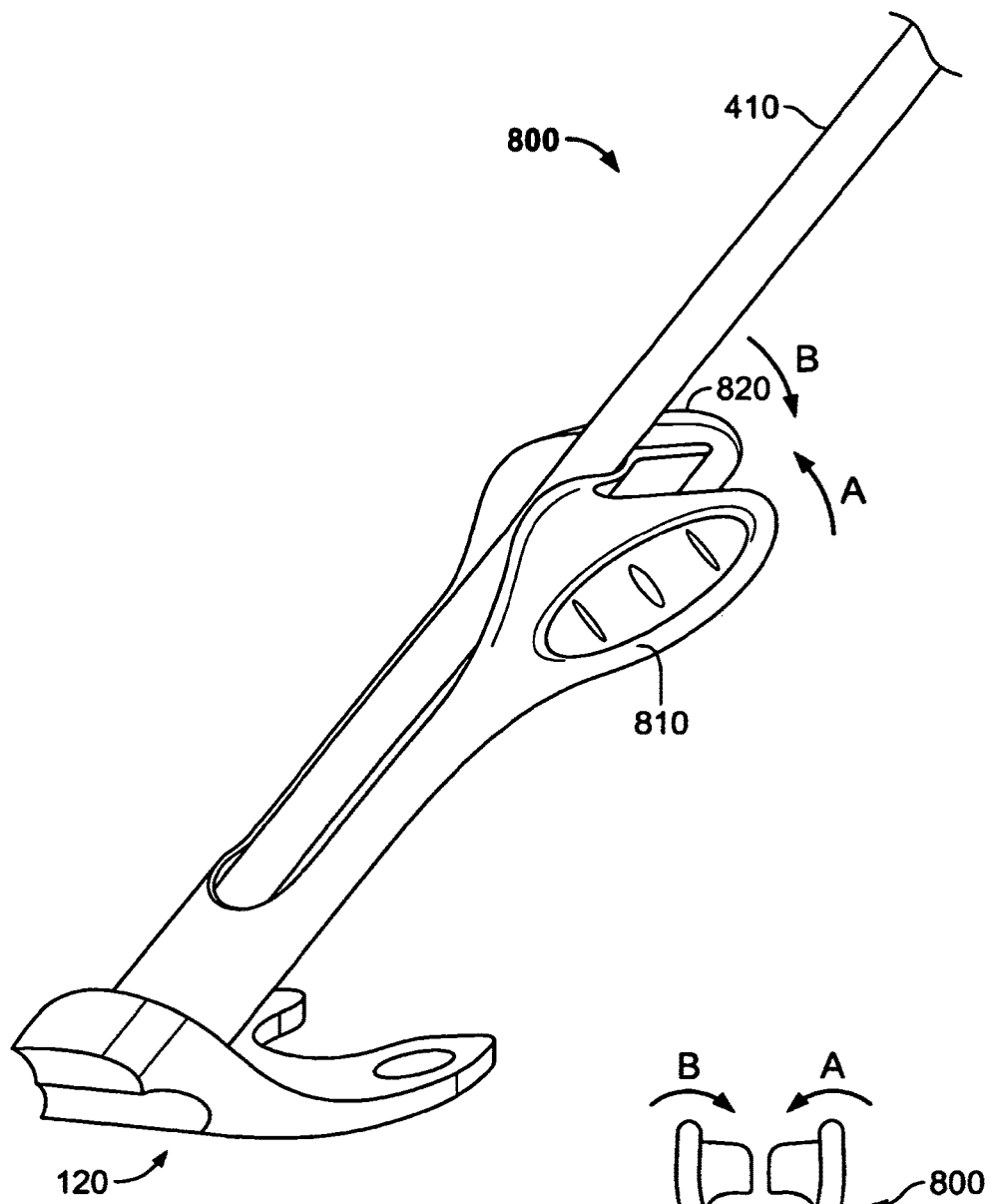
FIG. 8 is a perspective view of a locking member in accordance with an embodiment of the present disclosure shown in use.
Figure 8A:
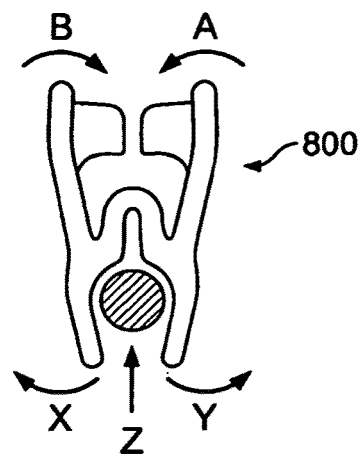
FIG. 8A is a cross-sectional view of the locking member of FIG. 8.

A locking member 800 will now be described with reference to FIGS. 8-8A. The locking member 800 is placeable within an appropriate channel of any suitable holder above in which an adjustment tool for adjusting the diameter of the ring 50 is receivable, e.g., channels 17, 217, 317. The locking member 800 may be securable within the channel to inhibit inadvertent rotation or free spinning of the adjustment tool and accidental adjustment of the diameter D of the ring 50. The locking member 800 includes a generally cylindrical section that is placeable within the channel in such a way that the locking member 800 may be frictionally engaged with the channel to inhibit rotation of the locking member 800. The locking member includes pinch tabs 810, 820 that are deflectable toward and against the directions indicated by directional arrows A, B. The tabs 810, 820 are biased toward one another at one end to frictionally engage the elongated shaft, e.g., rod 410 of an adjustment tool, and may thereby inhibit rotation or free spinning of the rod 410. As shown in FIG. 8A, the rod 410 is snap-fit in place between the tabs 810, 820 by pressing the rod 410 between the tabs 810, 820 in the direction indicated by arrow z, thereby spacing the tabs 810, 820 apart as indicated by arrows x, y. By pinching the opposite ends of the tabs 810, 820 together in the direction indicated by arrows A, B, the rod 410 is free to rotate. However, such rotation is inhibited if the opposite ends of the tabs 810, 820 are not pinched together. In this way, the locking member 800 may inhibit accidental adjustment of the ring 50.

Figure 9A:
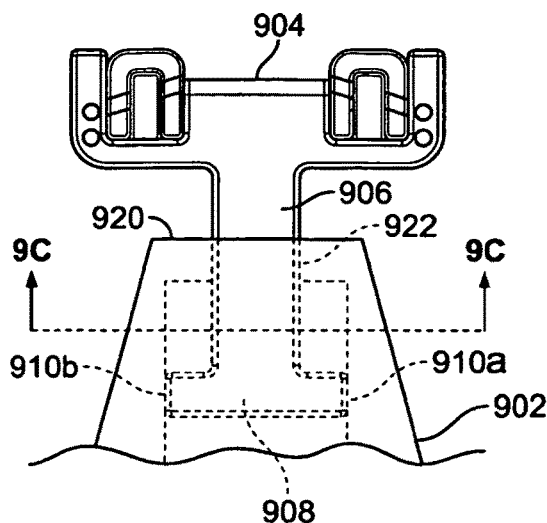
FIG. 9A is a top view of an annuloplasty ring holder in accordance with another embodiment of the present invention.
Figure 9B:
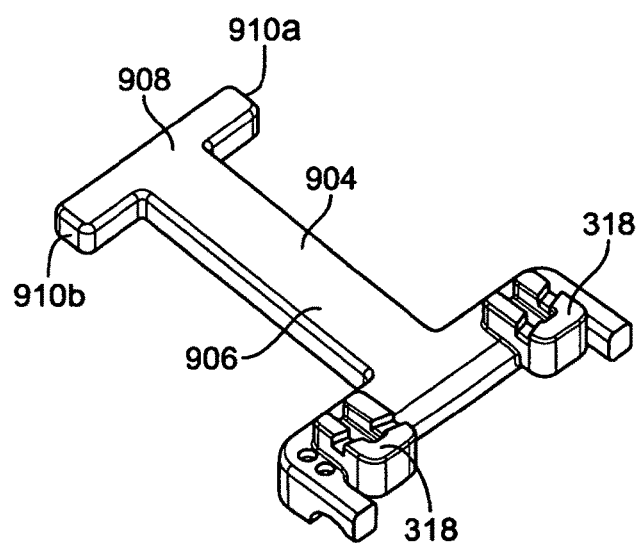
FIG. 9B is a perspective view of a component of the annuloplasty ring holder shown in FIG. 9A.
Figure 9C:
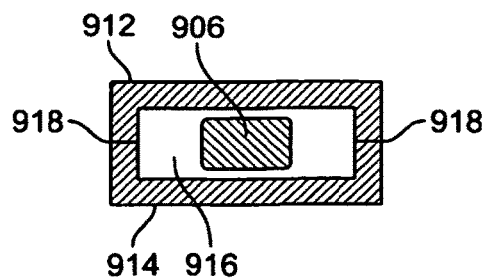
FIG. 9C is a cross-sectional view of the annuloplasty ring holder of FIG. 9A.

Referring now to FIGS. 9A-9C, another embodiment of an annuloplasty ring holder 900 is shown. The annuloplasty ring holder 900 includes a first or posterior member 902 and a second or anterior member 904. As best shown in FIG. 9B, the second member 904 has a somewhat similar construction to the second member 340 of the annuloplasty ring holder 300 shown in FIG. 4B. In the holder 900, the second member 904 includes a bar 906 terminating at a rectangular member 908 having lateral side members 910a, 910b which extend outwardly beyond the side edges of the bar 906.

As shown in FIGS. 9A, 9C, the first member 902 includes an upper segment 912 and a lower segment 914 which, when assembled, form a generally rectangular inner channel 916 adapted to slidingly receive in telescopic arrangement the rectangular member 908 of the second member 904. The upper and lower segments 912, 914 are generally formed with a u-shaped cross section so as to define the channel 916. The upper and lower segments 912, 914 are assembled by snap fitting the segments together along their mating edges 918 using any known mechanical-type fastening structure. The end 920 of the first member 902 is formed with a restricted opening 922 sized to accommodate reciprocal movement of the bar 906, while precluding complete withdrawing of the bar from the first member 902 by engagement with the lateral side members 910a, 910b. Accordingly, the upper and lower segments 912, 914 are snap-fit together about the bar 906 of the second member 904 to form a completed holder 900 which, when in use, will not separate. The remaining aspects and features of the holder 900 can be constructed in accordance with those aspects and features of the holders 100, 200, 300 previously described. For example, the first member 902 may include a neck member adapted for receiving an adjustment tool, and optionally, a channel adapted for receiving a positioning tool in the manner thus far described.

Another embodiment of an annuloplasty ring holder 950 will now be described with reference to FIG. 10. The annuloplasty ring holder 950 includes a posterior or first member 952 and an anterior or second member 954. As will be apparent, the holder 950 has features which are similar to those previously described with respect to the holders 100, 200, 300 and 900. The second member 954 includes an elongated rectangular bar 956 extending from a cross member 958. In one embodiment, the cross member 958 can be constructed for attaching the second member 954 to a ring 50 in the manner previously described.

In the embodiment shown, the cross member 958 includes apertures 960 to receive a suture for securing to a ring 50. The cross member 958 includes a centralized cutting block 964. The cutting block 964 is formed by two spaced apart members adapted to receive a scalpel for severing a suture which passes transversely therethrough. To facilitate a surgeon's placement of a scalpel, the cutting block may be bound by indicia, such as colored (e.g., black) boxes or other indicia, which provide a visual identification of the location of the cutting block. An upstanding protrusion or projection 968 is provided on the upper surface of bar 956 adjacent its terminal end opposite the cross member 958.

The first member 952 is formed from a body which includes a pair of spaced apart legs 970a, 970b which define an elongated open channel 972 therebetween. The legs 970a, 970b have inwardly facing ribs 974a, 974b to provide support for the bar 956 when received within the channel. A tab member 976 overlying the channel 972 has one end attached or formed integral with the first member 952. The tab member 976 is bound on opposite sides by elongated openings 978a, 978b extending between the tab member and the legs 970a, 970b, respectively. The construction of the tab member 976 and openings 978a, 978b render the tab member flexible. The underside of the tab member includes an elongated groove 980 bound at opposite ends by portions of the tab member 976. The bar 956 of the second member 954 is slidingly received within the channel 972 of the first member 952. As the bar enters the channel, the projection 968 initially engages the bottom of the tab member 976, so as to displace the tab member upwardly until the projection enters the groove 980. At that point, the tab member 976, due to its resilient nature, will be displaced downwardly into its original orientation, capturing the projection 968 within the groove 980. In this arrangement, the second member 954 is adapted to telescopically slide within the first member 952, being limited in movement distally and proximally by the projection 968 being captured within the groove 980. In an embodiment, the first and second members 952, 954 may be separated if desired by displacing the tab member 976 upwardly to allow the projection 968 to be disengaged from the groove 980. Accordingly, the first and second members 952, 954 telescopically move relative to one another within a common plane along a single axis of the holder 950.

The holder 950 may further include apertures 982 to accept a suture for securing the first member 952 to the ring 50. The suture may extend through a channel 989 provided on the tab member 976. A cutting block 986 can be formed on the tab member 976 by spaced apart legs which define a transverse opening intersecting the channel 989 and suture therein. As previously described, the cutting block 986 facilitates severing of the suture to enable removal of the holder 950 from ring 50. To facilitate identification of the cutting block 986, the spaced apart legs may be provided with appropriate indicia, such as colored or graphic designations in the manner previously described. The holder 950, likewise, may include a neck member 988 to accommodate an adjustment tool and optionally a positioning tool in the manner previously described. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, although the devices and systems are shown and described as being used for the repair and/or reconstruction of the mitral valve, the devices and systems may be used for the repair and/or reconstruction of other valves.

The invention claimed is:

1. An adjustable prosthetic anatomical system, comprising:
   an adjustable prosthetic anatomical device including an anterior region and a posterior region, the device being transitionable in a controlled manner from a first diameter to a second diameter and being adapted to remain at the second diameter after such transition;
   an adjustment tool including an elongated shaft directly engageable with the device to effect transitioning of the device from the first diameter to the second diameter; and
   a holder comprising:
      a first member operably attachable to the posterior region of the device;
      a neck member extending from the first member, the neck member including a channel in which the elongated shaft of the adjustment tool is receivable; and
      a second member operably attachable to the anterior region of the device, wherein the first member and the second member are engageable with one another and slidable telescopically relative to one another in response to adjustment of the device from the first diameter to the second diameter.

2. The system of claim 1, wherein the channel has a generally U-shaped configuration.

3. The system of claim 1, wherein the elongated shaft of the adjustment tool is detachable from the neck member while the adjustment tool is operably engaged with the device.

4. The system of claim 1, wherein the first member defines an elongated slot along a longitudinal axis, and the second member includes a pair of opposing tabs receivable within the elongated slot to secure the second member to the first member, whereby the first and second members are slideable relative to each other along the longitudinal axis.

5. The system of claim 1, wherein the first member and the second member are each securable to the device by a length of suture, and the first and second members each include a cutting block to facilitate cutting of the length of suture.

6. The system of claim 5, wherein the cutting blocks are aligned along a common axis.

7. The system of claim 1, wherein the neck member further comprises a second channel configured and adapted to receive a positioning tool to facilitate positioning of the holder.

8. The system of claim 1, wherein the first member includes a longitudinally extending channel and the second member includes a longitudinally extending bar, the bar being translatable through the channel along a single axis of the first and second members.

9. The system of claim 8, wherein the first member and the second member are operably coupled to one another by a length of suture.

10. The system of claim 1, further comprising a positioning tool including a rod, the neck member including a channel adapted for receiving the rod.

11. The system of claim 10, wherein the rod is formed from a malleable material.

12. The system of claim 1, wherein the neck member further includes a second channel adapted for receiving a positioning tool.

13. The system of claim 12, further comprising a positioning tool assembled to the holder in an assembled position, the positioning tool including an elongated shaft, wherein the elongated shaft of the adjustment tool and the elongated shaft of the positioning tool are substantially parallel to one another in the assembled position.

14. The system of claim 13, wherein the positioning tool includes a handle having a proximal end and a distal end, the handle defining a groove extending between the proximal and distal ends and adapted to rotationally receive the elongated shaft of the adjustment tool therein, the elongated shaft of the positioning tool extending distally from the distal end of the handle.

15. The system of claim 14, wherein the handle includes at least one aperture adapted to receive suture therethrough to inhibit separation of the elongated shaft of the adjustment tool from the groove of the handle.

16. The system of claim 1, further comprising a locking mechanism including a cylindrical section that is securable within the channel, the locking mechanism releasably engaging the elongated shaft of the adjustment tool.

17. The system of claim 16, wherein the locking mechanism selectively inhibits rotation of the elongated shaft of the adjustment tool.

18. An adjustable prosthetic anatomical device holder, comprising:
   a first member operably attachable to a posterior region of an adjustable prosthetic anatomical device;
   a second member operably attachable to an anterior region of the device, the first member and the second member being engageable with one another and slidable telescopically relative to one another in response to adjustment of the device from a first diameter to a second diameter larger than the first diameter;

a neck member on the first member, the neck member defining a first channel and a second channel;

an adjustment tool received in the first channel, the adjustment tool being effective to transition the device from the first diameter to the second diameter; and a positioning tool received in the second channel, the positioning tool facilitating positioning of the holder.

19. The holder of claim 18, wherein the first channel has a generally U-shaped configuration.

20. The holder of claim 18, wherein the first member defines an elongated slot along a longitudinal axis, and the second member includes a pair of opposing tabs receivable within the elongated slot to secure the second member to the first member, whereby the first and second members are slideable relative to each other along the longitudinal axis.

21. The holder of claim 18, wherein the first member and the second member each include an opening for receiving a length of suture for securing the first and second members to the device.

22. The holder of claim 21, wherein the first and second members each include a cutting block to facilitate cutting of the length of suture.

23. The holder of claim 18, wherein the first member includes a longitudinally extending channel and the second member includes a longitudinally extending bar, the bar being translatable within the channel along a single axis of the first and second members.

24. The holder of claim 23, further including a length of suture tethering the first member to the second member.

25. The holder of claim 18, wherein the first member includes sections adapted to be snap fitted together with the second member.

26. The holder of claim 18, wherein the first and second members move relative to one another along a common plane.

27. The holder of claim 18, wherein the first and second members move relative to one another along a single axis of the holder.

28. The holder of claim 18, wherein the second member includes a bar having a projection adapted to be received within a groove provided in the first member.

29. An adjustable prosthetic anatomical system, comprising:

an adjustable prosthetic anatomical device including an anterior region and a posterior region, the device being transitionable from an initial diameter to a second diameter larger than the initial diameter;

an adjustment tool directly engageable with the device to effect transitioning of the device from the first diameter to the second diameter; and a holder comprising:
    a first member operably attachable to the posterior region of the device; and
    a neck member extending from the first member, the neck member including a channel in which the elongated shaft of the adjustment tool is receivable; and
    a second member operably attachable to the anterior region of the device, wherein the first member and the second member are engageable with one another and slidable telescopically relative to one another in response to the transition of the device from the initial diameter to the second diameter.

30. An adjustable prosthetic anatomical system, comprising:

an adjustable prosthetic anatomical device including an anterior region and a posterior region, the device being transitionable in a controlled manner from a first diameter to a second diameter and being adapted to remain at the second diameter after such transition;

an adjustment tool including an elongated shaft directly engageable with the device to effect transitioning of the device from the first diameter to the second diameter; and a holder comprising:
    a first member operably attachable to the posterior region of the device; and
    a second member operably attachable to the anterior region of the device, wherein the first member and the second member are engageable with one another and slidable telescopically relative to one another in response to adjustment of the device from the first diameter to the second diameter.

31. An adjustable prosthetic anatomical system, comprising:

an adjustable prosthetic anatomical device including an anterior region and a posterior region, the device being transitionable from an initial diameter to a second diameter larger than the initial diameter;

an adjustment tool directly engageable with the device to effect transitioning of the device from the first diameter to the second diameter; and a holder comprising:
    a first member operably attachable to the posterior region of the device; and
    a second member operably attachable to the anterior region of the device, wherein the first member and the second member are engageable with one another and slidable telescopically relative to one another in response to the transition of the device from the initial diameter to the second diameter.

* * * * *